(12) United States Patent
Kase et al.

(10) Patent No.: US 8,227,010 B2
(45) Date of Patent: Jul. 24, 2012

(54) PROCESS FOR PRODUCING OIL AND FAT RICH IN DIACYLGLYCEROL

(75) Inventors: Minoru Kase, Kamisu (JP); Masao Shimizu, Sumida-ku (JP); Junya Moriwaki, Sumida-ku (JP)

(73) Assignee: Kao Corporation, Tokyo (JP)

( * ) Notice: Subject to any disclaimer, the term of this patent is extended or adjusted under 35 U.S.C. 154(b) by 590 days.

(21) Appl. No.: 12/249,331

(22) Filed: Oct. 10, 2008

(65) Prior Publication Data
US 2010/0092650 A1 Apr. 15, 2010

(51) Int. Cl.
A23D 9/007 (2006.01)
A23D 9/02 (2006.01)
C11B 3/10 (2006.01)

(52) U.S. Cl. ........................ 426/601; 426/417
(58) Field of Classification Search .......... 426/601–609, 426/417
See application file for complete search history.

(56) References Cited

U.S. PATENT DOCUMENTS

| | | | | |
|---|---|---|---|---|
| 6,337,414 | B1* | 1/2002 | Sugiura et al. | 554/174 |
| 7,126,019 | B2 | 10/2006 | Bloom et al. | |
| 7,867,538 | B2* | 1/2011 | Binder et al. | 426/423 |
| 2006/0258872 | A1* | 11/2006 | Kase et al. | 554/174 |
| 2007/0141222 | A1* | 6/2007 | Binder et al. | 426/601 |
| 2008/0069932 | A1* | 3/2008 | Kohori et al. | 426/541 |
| 2010/0092650 | A1* | 4/2010 | Kase et al. | 426/601 |

FOREIGN PATENT DOCUMENTS

| | | |
|---|---|---|
| JP | 63-133992 | 6/1988 |
| JP | 64-071495 | 3/1989 |
| JP | 4-261497 | 9/1992 |
| JP | 10-176181 | 6/1998 |
| JP | 11-123097 | 5/1999 |
| JP | 2007-503524 | 2/2007 |
| WO | WO 03/029392 A1 | 4/2003 |

OTHER PUBLICATIONS

Schultz, H. W. 1962. Lipids and their Oxidation. The AVI Publishing Company, Inc., Westport, CT. p. 13.*
Swern, D., editor. 1982. Baileys Industrial Oil and Fat Products, vol. 2, 4th edition. John Wiley & Sons, New York. p. 134-143, 322-325.*
Holm, U. et al. 1957. JAOCS 34:607.*
Kristensen, J. B. et al. 2005. JAOCS 82(5)329.*
Nkpa, N. et al. 1989. JAOCS 66(2)218.*
Tan, C. P. et al. 2001. JAOCS 78(12)1227.*
Swern, D. 1982. Bailey's Industrial Oil and Fat Products, vol. 2, 4$^{th}$ edition. John Wiley & Sons, New York. p. 110-111.*
U.S. Appl. No. 12/995,096, filed Nov. 29, 2010, Kase, et al.
U.S. Appl. No. 12/672,285, filed Feb. 5, 2010, Kase, et al.

* cited by examiner

Primary Examiner — Carolyn Paden
(74) Attorney, Agent, or Firm — Oblon, Spivak, McClelland, Maier & Neustadt, L.L.P.

(57) ABSTRACT

The present invention relates to a process for producing oils and fats rich in diacylglycerol by subjecting fatty acids which are obtainable by hydrolyzing raw material oils and fats, to esterification with glycerin, wherein the process comprises decreasing an anisidine value of greater than 6 of the raw material oils and fats or reaction intermediates, by 20% or more. By using the process of the present invention, even in the case of using a raw material having an anisidine value which is likely to increase in the production processes for raw material oils and fats or for oils and fats rich in diacylglycerol, the stability of the final product oils and fats rich in diacylglycerol is enhanced, and coloration is suppressed, so that products having excellent external appearance can be obtained.

14 Claims, No Drawings

PROCESS FOR PRODUCING OIL AND FAT RICH IN DIACYLGLYCEROL

FIELD OF THE INVENTION

The present invention relates to a process for producing oils and fats rich in diacylglycerol.

BACKGROUND OF THE INVENTION

Oils and fats containing diacylglycerol in high concentrations are known to have physiological effects such as being less accumulative in the body (see Patent Document 1), and are widely used as edible oil. In regard to the processes for producing diacylglycerol, there are known processes involving an esterification reaction based on a chemical method or an enzymatic method, using fatty acids and glycerin as the raw materials (see Patent Document 2), a process of performing glycerolysis based on a chemical method or an enzymatic method, using oils and fats and glycerin as the raw materials, and the like (see Patent Documents 3 and 4).

Among the above-described processes for production, in one step in the process involving glycerolysis using oils and fats and glycerin as the raw materials, the reaction is completed, whereas in the process involving an esterification reaction using fatty acids and glycerin as the raw materials, above all, the fatty acids used as a raw material require a process of hydrolyzing oils and fats. In this case, since the hydrolysis reaction of oils and fats is usually carried out under high temperature and high pressure conditions, coloration may occur in some cases, depending on the conditions. Furthermore, in order to increase the purity of diacylglycerol in the reaction product, it is preferable to enhance the concentration of the raw material fatty acids. For that reason, it may become necessary to perform a distillation treatment after the hydrolysis of oils and fats (see Patent Document 5).

On the other hand, there are cases where, if a distillation treatment is performed after hydrolysis of oils and fats, the yield is decreased, or useful components present in plant oils, such as plant sterols or antioxidative components, are lost. Therefore, there has also been suggested a process in which the hydrolysate obtained after the hydrolysis of oils and fats is not distilled, but glycerin is added thereto, and an esterification reaction is performed (see Patent Document 6).

Moreover, in the process for producing diacylglycerol, a decoloration treatment is carried out, typically in the final stage, by using an adsorbent such as activated clay (see Patent Document 7).

[Patent Document 1] JP-A-10-176181
[Patent Document 2] JP-A-01-71495
[Patent Document 3] WO 03/29392
[Patent Document 4] JP-A-63-133992
[Patent Document 5] JP-A-2007-503524
[Patent Document 6] JP-A-11-123097
[Patent Document 7] JP-A-04-261497

SUMMARY OF THE INVENTION

The present invention provides a process for producing oils and fats rich in diacylglycerol, by subjecting fatty acids which are obtainable by hydrolyzing raw material oils and fats, to an esterification reaction with glycerin, the process comprising decreasing an anisidine value of greater than 6 of the raw material oils and fats or the diacylglycerol production intermediates, by 20% or more.

DETAILED DESCRIPTION OF THE INVENTION

The present invention is designed to prevent coloration, when oils and fats rich in diacylglycerol are produced using oils and fats as raw materials, by subjecting fatty acids obtainable by hydrolyzing the fats and oils, to esterification with glycerin. In the conventional technologies as described above, the problem of coloration of fatty acids occurring upon hydrolysis of raw material oils and fats under high temperature and high pressure conditions, is solved by carrying out a distillation treatment. However, the inventors of the present invention found that even though oils and fats rich in diacylglycerol are produced using the fatty acids obtained in that manner, there still are cases where the final products are colored.

The present inventors conducted an investigation on the elements causative of coloration, and as a result, the inventors found out that regarding the coloration in final products, merely eliminating the materials which directly cause coloration, from the raw material oils and fats or from the diacylglycerol production intermediates is insufficient, and the anisidine value of the raw material oils and fats or the diacylglycerol production intermediates exert direct influence on the coloration, thus completing the present invention.

The fatty acids used in the present invention are fatty acids obtainable by hydrolyzing oils and fats. As for the raw material oils and fats, any of plant oils and fats and animal oils and fats may be used. Specific examples of the raw material include rapeseed oil, sunflower oil, corn oil, soybean oil, linseed oil, rice oil, safflower oil, cottonseed oil, beef tallow, fish oil, and the like. Furthermore, products obtained by fractionating or mixing these oils and fats, or products having the fatty acid composition adjusted by hydrogenation, transesterification reaction or the like, may also be used. However, products which have not been hydrogenated are preferred from the viewpoint of reducing the content of trans-unsaturated fatty acids in the constituent fatty acids in the raw material oils and fats.

According to an embodiment of the present invention, the raw material oils and fats are preferably processed such that oil is expressed from the respective plants or animals used as the oil source, and then solid fraction other than the oil fraction is removed by filtration, centrifugation or the like. Subsequently, it is preferable to add water, and optionally an additional acid to the resultant oil fraction to mix therewith, and then to degum the mixture by separating the gum components by centrifugation or the like. Furthermore, it is preferable to deacidify the raw material oils and fats by adding an alkali to the raw material oils and fats to mix, then washing the mixture with water, and dehydrating the resultant product. Moreover, it is preferable to decolor the raw material oils and fats by contacting the oils and fats with an adsorbent such as activated clay, and then separating the adsorbent by filtration or the like. It is preferable that these treatments be carried out in the above-described order, but the order may be modified. In addition to that, it is also desirable, in order to remove the wax fraction, to perform wintering which separates the solid fraction at a low temperature. The raw material oils and fats may also be subjected to deodorization, if necessary, by contacting the oils and fats with steam under reduced pressure. In this case, it is preferable to maintain the thermal history as low as possible, from the viewpoint of reducing the content of trans-unsaturated fatty acids in the constituent fatty acids of the oils and fats. In regard to the conditions for the deodorization process, the temperature is preferably controlled to 300° C. or lower, and more preferably to 270° C. or lower, and the time is preferably limited to 10 hours or less, and more preferably to 5 hours or less.

In the present invention, the hydrolysis of oils and fats may be carried out by any of a high temperature and high pressure degradation method, and an enzymatic degradation method.

The hydrolysis operation according to the method for high temperature and high pressure degradation of oils and fats can be performed in a batch mode, in a continuous mode, or in a semi-continuous mode, while the supply of the raw material oils and fats and water into the apparatus may be achieved by either the co-current mode or the counter-current mode. In regard to the raw material oils and fats and water to be supplied to the hydrolysis reaction apparatus, it is preferable to use raw material oils and fats and water which have been degassed or deoxidized in advance as necessary, from the viewpoint of suppressing oxidation of the oils and fats.

In regard to the hydrolysis operation according to the high temperature and high pressure degradation method, it is preferable to perform hydrolysis by adding water in an amount of 10 to 250 parts by weight, relative to 100 parts by weight of oils and fats, under the conditions of a temperature of 200 to 270° C. and a pressure of 2 to 8 MPa, over 0.1 to 6 hours. From the viewpoints of the industrial productivity of fatty acids, and suppression of decoloration and the generation of trans-unsaturated fatty acids, it is preferable to maintain the temperature at 210 to 265° C., and more preferably at 215 to 260° C. The amount of water based on 100 parts by weight of oils and fats is set, from the same point of view, more preferably to 15 to 150 parts by weight, and even more preferably to 20 to 120 parts by weight. The pressure is also set, from the same point of view, more preferably to 2 to 7 MPa, and even more preferably to 2.5 to 6 MPa. Furthermore, the reaction time is set, from the same point of view, more preferably to 0.2 to 5 hours, and even more preferably to 0.3 to 4 hours.

As for a preferred reaction apparatus, there may be mentioned, for example, a Colgate-Emery type oil and fat splitting column in a counter-current mode, equipped with a hydrolysis reaction tank having a capacity of 7 to 40 m$^3$ (for example, IHI Corporation). Furthermore, for small quantity degradation in a laboratory scale, a commercially available autoclave apparatus (for example, Nitto Kouatsu Co., Ltd.) may also be used as the hydrolysis reaction tank.

It is desirable that the hydrolysis reaction of oils and fats under high temperature and high pressure conditions be managed by means of the fatty acid concentration, and be terminated at a point in time where a predetermined fatty acid concentration is reached. Here, the "fatty acid concentration" according to the present invention refers to the value determined by measuring the acid value of fatty acids and the fatty acid composition, and applying the measured values to the following formula (1), according to the procedure described in "Knowledge on Oil and Fat Products" (published by Saiwaishobo, Ltd.). Additionally, the acid value is measured according to the procedure described in "Acid Value (2.3.1-1996)" in "Standard Methods for the Analysis of Fats, Oils, and Related Materials," edited by the Japan Oil Chemists' Society (2003).

$$\text{Fatty acid concentration (wt \%)} = x \times y / 56.1 / 10 \qquad (1)$$

(x=acid value [mg KOH/g], y=average molecular weight determined from the fatty acid composition)

The hydrolysis operation according to the method for high temperature and high pressure degradation of oils and fats is preferably carried out until the fatty acid concentration reaches 70% by weight or higher, more preferably 70 to 99% by weight, and even more preferably 75 to 98% by weight, from the viewpoints of the purity of diacylglycerol after the esterification reaction, industrial productivity, good external appearance, and suppression of the generation of trans-unsaturated fatty acids. As a result of the hydrolysis, color C (according to the Lovibond method) is preferably 35 or less, more preferably 1 to 30, and even more preferably 5 to 25, and the content of trans-unsaturated fatty acids in the constituent fatty acids is preferably 0 to 1.5% by weight, more preferably 0.1 to 1.2% by weight, and even more preferably 0.2 to 0.7% by weight. Furthermore, the content of monoglyceride is preferably 1 to 20% by weight, more preferably 1 to 15% by weight, and even more preferably 3 to 10% by weight.

The fatty acids obtained by hydrolysis may be used directly, or alternatively, may be used after being subjected to purification by distillation, adjustment of the fatty acid composition by wintering, or the like.

In the hydrolysis according to the enzymatic degradation method, the enzyme used for oil and fat degradation is preferably a lipase. As for the lipase, not only animal-derived lipases and plant-derived lipases, but also commercially available, microorganism-derived lipases, and immobilized enzymes prepared by immobilizing lipases, may be used. Examples of the enzyme for oil and fat degradation include lipases of microbial origin, such as of genus *Rhizopus*, genus *Aspergillus*, genus *Chromobacterium*, genus *Mucor*, genus *Pseudomonas*, genus *Geotrichum*, genus *Penicillium*, or genus *Candida*, and animal lipases such as pancreatic lipases. In order to obtain a high degradation rate, a lipase having no positional specificity (random type) is preferred, and in terms of the microbial origin, genus *Pseudomonas*, genus *Candida* and the like are preferred.

According to another embodiment of the present invention, it is preferable for the hydrolysis of oils and fats according to the enzymatic degradation method, to use an immobilized enzyme in which the enzyme is immobilized on a carrier, from the viewpoint of effectively using the enzyme activity. As for the immobilized enzyme, it is preferable to use a lipase supported on a carrier for immobilization. Examples of the carrier for immobilization include inorganic carriers such as celite, diatomaceous earth, kaolinite, silica gel, molecular sieves, porous glass, activated carbon, calcium carbonate, ceramics and powdered ceramics; organic polymers such as, polyvinyl alcohol, polypropylene, chitosan, ion exchange resins, hydrophobic adsorptive resins, chelating resins, and synthetic adsorptive resins; and the like. However, in view of water retaining power, ion exchange resins are preferred. Also, among the ion exchange resins, porous resins are preferred from the viewpoint that the resins have large surface areas, and thus can adsorb a large quantity of lipase.

According to another embodiment of the present invention, the hydrolysis operation according to the method for enzymatic degradation of oils and fats may be carried out in a batch mode, in a continuous mode, or in a semi-continuous mode, and the supply of oils and fats and water into the apparatus may employ either the co-current mode or the counter-current mode. The oils and fats supplied into the hydrolysis reaction apparatus are preferably degassed or deoxidized in advance, from the viewpoint of suppressing the oxidation of fatty acids.

The hydrolytic activity of the immobilized enzyme is preferably 20 U/g or higher, more preferably in the range of 100 to 10000 U/g, and even more preferably in the range of 500 to 5000 U/g. Here, 1 U of an enzyme indicates the degradation capacity of an enzyme to produce 1 µmol of free fatty acids in one minute, when a mixture liquid of oils and fats:water=100: 25 (mass ratio) is hydrolyzed for 30 minutes at 40° C., while mixing the mixture liquid while stirring.

The amount of the immobilized enzyme used in the reaction of the enzymatic degradation method may be appropriately determined by taking into consideration the enzyme activity, but the amount is preferably 0.01 to 30 parts by weight, more preferably 0.1 to 20 parts by weight, and even more preferably 1 to 10 parts by weight, based on 100 parts by weight of the raw material oils and fats to be degraded. Furthermore, the amount of water is preferably 10 to 200 parts by weight, more preferably 20 to 100 parts by weight, and even more preferably 30 to 80 parts by weight, based on 100 parts by weight of the raw material oils and fats to be degraded. The water may be freely selected from any of distilled water, ion-exchanged water, degassed water, tap water, well water, and the like. Other water-soluble components such as glycerin may also be incorporated therein. If necessary, a buffer solution at pH 3 to 9 may also be used so as to maintain the stability of enzyme.

The reaction temperature is preferably set to a temperature at which the enzyme activity is more effectively manifested, and free fatty acids generated by degradation do not turn into crystals, that is, 0 to 70° C., and more preferably 20 to 50° C. It is also preferable that the reaction be carried out in the presence of an inert gas such as nitrogen gas, carbon dioxide gas or helium gas, so that contact with air can be avoided as far as possible.

The hydrolysis reaction in the method for enzymatic degradation of oils and fats may be managed by means of the concentration of produced fatty acids, and terminated at a time point where a predetermined fatty acid concentration is reached, as in the case of hydrolysis according to the high temperature and high pressure degradation method. That is, it is preferable that the hydrolysis according to the method for enzymatic degradation of oils and fats be carried out until the fatty acid concentration reaches 70% by weight or higher, more preferably 70 to 99% by weight, and even more preferably 75 to 98% by weight, from the viewpoints of the purity of diacylglycerol obtained after the esterification reaction, industrial productivity, good external appearance, and the generation of trans-unsaturated fatty acids. Furthermore, it is preferable that hydrolysis be carried out until the monoacylglycerol concentration reaches 1 to 20% by weight, more preferably 1 to 15% by weight, and even more preferably 2 to 10% by weight.

The fatty acids obtained by hydrolysis may be used directly, or alternatively, may be used after being subjected to purification by distillation, adjustment of the fatty acid composition by wintering, or the like.

In the case of distilling the fatty acids obtained by hydrolysis, it is preferable to set the operation temperature at 100 to 300° C., more preferably at 120 to 250° C., and even more at 150 to 250° C., and to set the pressure at 0.133 to 2660 Pa, and more preferably at 1.33 to 1330 Pa, from the viewpoints of the fatty acid concentration, industrial productivity, good external appearance, and suppression of the generation of trans-unsaturated fatty acids. It is also preferable to perform the distillation until the fatty acid concentration reaches 85% by weight or higher, more preferably 90 to 100% by weight, and even more preferably 95 to 99.9% by weight. Furthermore, it is preferable that the monoglyceride content be 0 to 15% by weight, more preferably 0 to 10% by weight, and even more preferably 0.1 to 5% by weight.

After distilling the fatty acids obtained by hydrolysis, if wintering is to be carried out, it is preferable to carry out the operation by a spontaneous fractionation method. The spontaneous fractionation method refers to a method of cooling the feedstock fatty acids to be treated, without adding water in an amount necessary for phase separation and without using a solvent, to thus perform solid-liquid separation of precipitated solid components. As for the spontaneous fractionation method, it is desirable to carry out the cooling while stirring, if necessary. Furthermore, as the means for solid-liquid separation, filtration, centrifugation, settling separation, and the like are used. The spontaneous fractionation method according to the present invention is preferably performed by adding a crystal controlling agent to the feedstock fatty acids before the precipitation of crystals. The crystal controlling agent is not particularly limited, but polyhydric alcohol fatty acid esters are preferred. For example, sucrose fatty acid esters, sorbitan fatty acid esters, propylene glycol fatty acid esters, organic acid monoglycerides, glycerin fatty acid esters, polyglycerin fatty acid esters and the like, known as food additives, may be mentioned. Among others, polyglycerin fatty acid esters are preferred. The crystal controlling agent may be used in combination of two or more species, and the amount of addition thereof is preferably about 0.001 to 5% by weight, and more preferably 0.05 to 1% by weight, with respect to the feedstock fatty acids.

In the case of using a polyglycerin fatty acid ester as the crystalline controlling agent, it is preferable to mix and dissolve the ester at a temperature higher than the clear melting point of the polyglycerin fatty acid ester, so that the ester can be completely dissolved in the feedstock fatty acids. The cooling time, cooling temperature and the retention time after this mixing and dissolving vary in accordance with the amount of feedstock, cooling ability and the like, and may be appropriately selected based on the composition of the feedstock fatty acids. For example, in the case of soybean fatty acid, the time for cooling to −3° C. is about 1 to 30 hours, and preferably about 3 to 20 hours, while the retention time is about 0 to 24 hours, and preferably about 1 to 10 hours. The cooling treatment may be performed in a batch mode, or in a continuous mode. The cooling operation is preferably carried out under the conditions such that the average particle size of the precipitated crystals would be 100 μm or larger, and particularly 150 μm or larger.

In the present invention, the process for esterifying fatty acids and glycerin may be carried out by any of a chemical method or an enzymatic method, but it is preferable to perform the esterification reaction by the enzymatic method, from the viewpoints of suppressing the generation of trans-unsaturated fatty acids, enabling adjustment of the fatty acid composition of the products, and increasing the purity of diacylglycerol.

In regard to the enzyme used in the esterification reaction, it is preferable to use a lipase, but particularly in the case of aiming at the production of functional oils and fats, such as diacylglycerol, there may be mentioned lipases derived from genus *Rhizopus*, genus *Aspergillus*, genus *Mucor*, genus *Pseudomonas*, genus *Geotrichum*, genus *Penicillium*, genus *Candida*, and the like, which are likely to selectively synthesize diacylglycerol.

Furthermore, in regard to the enzyme used in the esterification reaction, it is preferable to use an immobilized enzyme in terms of costs.

In the case of performing the esterification reaction by the enzymatic method, it is preferable to set the reaction temperature at 0 to 100° C., more preferably 20 to 80° C., and even more preferably 30 to 80° C., from the viewpoints of enhancing the reaction rate and suppressing deactivation of the enzyme.

In the case of performing the esterification reaction by a chemical method, it is preferable to set the reaction temperature at 100 to 300° C., and more preferably 150 to 250° C., from the viewpoints of enhancing the reaction rate and suppressing the generation of trans-unsaturated fatty acids. It is also preferable to use an alkali such as sodium hydroxide or calcium hydroxide, or an acid such as an organic acid, or a salt thereof, as a catalyst, from the viewpoints of enhancing the reaction rate and making the color of the reaction oil good.

Furthermore, in the case of performing the esterification reaction by an enzymatic method, it is preferable to carry out dehydration under reduced pressure at the time of reaction, from the viewpoint of maintaining the content of diacylglycerol high in the reaction oil. In the case of performing the esterification reaction by a chemical method, it is preferable to carry out dehydration by passing a carrier gas at the time of reaction, from the viewpoint of maintaining the content of diacylglycerol high in the reaction oil.

In regard to the feed ratio of the raw materials at the time of performing the esterification reaction, it is preferable to adjust the ratio of the number of moles of a fatty acid group to the number of moles of a glycerin group to 0.2 to 10, more preferably 0.3 to 0.8, even more preferably 0.5 to 6, and even more preferably 0.5 to 4, from the viewpoints that the composition of the reaction oil becomes optimal (the residual amounts of fatty acids and glycerin in the reaction oil, and the amount of generation of monoacylglycerol or triacylglycerol are suppressed so that the burden of distillation is reduced, and at the same time, the reaction oil becomes rich in diacylglycerol, thereby the production efficiency being increased). Hereinafter, the ratio of the number of moles of this glycerin group to the number of moles of fatty acid groups will be represented by "FA/GLY". The FA/GLY is represented by the following formula.

FA/GLY=(number of moles of fatty acids+number of moles of a lower alcohol ester of a fatty acid+number of moles of monoacylglycerol+number of moles of diacylglycerol×2+number of moles of triacylglycerol×3)/(number of moles of glycerin+number of moles of monoacylglycerol+number of moles of diacylglycerol+number of moles of triacylglycerol)

The FA/GLY value is appropriately selected in accordance with the form of reaction. For example, in the case of the esterification reaction using an enzyme, the value is preferably 1 to 3, and more preferably 1.5 to 2.5 from the viewpoint that the composition of the reaction oil becomes optimum. In the esterification reaction in the chemical method, the value is preferably 0.3 to 3, and more preferably 0.4 to 2.2, from the viewpoint that the composition of the reaction oil becomes optimum.

The reaction oil obtained after performing the esterification reaction contains, together with diacylglycerol, fatty acids and glycerin as unreacted reactants, and triacylglycerol and monoacylglycerol as side products. According to the embodiment of the present invention, it is preferable to remove fatty acids, glycerin and monoacylglycerol from the reaction oil obtained after the esterification reaction, by a distillation operation. These unreacted reactants or side products may also be recovered and recycled.

According to an embodiment of the present invention, the content of monoacylglycerol in the reaction oil obtained after performing the esterification reaction is preferably 2 to 60% by weight, more preferably 3 to 50% by weight, even more preferably 5 to 50% by weight, and even more preferably 10 to 50% by weight, in terms of maintaining the diacylglycerol content high in the product, reducing the burden of distillation, and enhancing the reaction efficiency. Furthermore, the content of diacylglycerol in the esterified reaction oil is preferably 10 to 90% by weight, more preferably 20 to 80% by weight, even more preferably 30 to 70% by weight, and even more preferably 30 to 60% by weight, in terms of maintaining the diacylglycerol content high in the product, reducing the burden of distillation, and enhancing the reaction efficiency.

According to an embodiment of the present invention, in order to remove fatty acids, glycerin and monoacylglycerol from the reaction oil obtained after the esterification reaction by a distillation operation, it is preferable to perform the distillation operation such that the monoacylglycerol content in the oils and fats obtained after distillation would be in the range of 0.1 to 15% by weight, in terms of maintaining the diacylglycerol content high, and it is more preferable to obtain a monoacylglycerol content in the oils and fats in the range of 0.1 to 10% by weight, more preferably 0.1 to 8% by weight, even more preferably 0.2 to 8% by weight, and even more preferably 0.3 to 8% by weight. The amount of oil fraction to be recovered may vary depending on the composition of the reaction oil, but it is preferable to have an amount 0.5- to 1.5-fold by weight, more preferably 0.6- to 1.4-fold by weight, and even more preferably 0.6- to 1.2-fold by weight, of the components other than diacylglycerol and triacylglycerol in the reaction oil, from the viewpoints of setting the monoacylglycerol content in the oils and fats obtained after the distillation in the range of 0.1 to 15% by weight, increasing the yield of diacylglycerol, and preventing an excess amount of oil fraction from being recycled. Furthermore, it is preferable to obtain the monoacylglycerol content in the deacidified oil obtained after the distillation to be 0.01- to 0.8-fold by weight of the monoacylglycerol content in the reaction oil, from the viewpoint of maintaining the diacylglycerol content high in the product, and it is more preferable to have the monoacylglycerol content to be 0.02- to 0.6-fold by weight, and more preferably 0.03- to 0.5-fold by weight.

For the conditions for distillation, the pressure is preferably 0.01 to 300 Pa, more preferably 0.1 to 200 Pa, and even more preferably 0.2 to 100 Pa, in view of reducing the facility costs or operating costs, enhancing the distillation capacity, allowing an optimum distillation temperature to be selected, and suppressing an increase in the trans-unsaturated fatty acids or thermal deterioration caused by the thermal history. The temperature is preferably 140 to 280° C., more preferably 150 to 260° C., and even more preferably 160 to 250° C., from the viewpoint of suppressing an increase in the trans-unsaturated fatty acids. The retention time is preferably 0.1 to 30 minutes, more preferably 0.2 to 20 minutes, and even more preferably 0.2 to 10 minutes, from the viewpoint of suppressing an increase in the trans-unsaturated fatty acids. Here, the retention time refers to an average retention time taken during the period in which the temperature of the oils and fats reaches the distillation temperature.

It is preferable that the conditions for distillation which render the monoacylglycerol content in the oils and fats obtained after the distillation to be in the range of 0.1 to 15% by weight, be established based on the vapor pressure curves of the respective components. Here, the vapor pressure curve means a curve showing the vapor pressure of a substance at varying temperatures. It is preferable that the temperature and pressure of the distillation residues (oils and fats obtained after distillation) at the time point of completion of the distillation process (in the case of continuous distillation, the outlet of the distillation process), be set to lie between the vapor pressure curve of monoacylglycerol and the vapor pressure curve of diacylglycerol. In the case of performing distillation at a certain operation pressure, it is preferable to control the amount of heating, such that the temperature of the distillation residues (oils and fats obtained after distillation) at the time point of completion of the distillation process (in the case of continuous distillation, the outlet of the distillation process), is higher than the evaporation temperature of monoacylglycerol at that pressure, and lower than the evaporation temperature of diacylglycerol at that pressure. Furthermore, the distillation conditions may be established by performing distillation calculation in accordance with the format of the distillation apparatus in use, using the vapor pressure curves of the respective components and the formula for the estimation of the vapor-liquid equilibrium relationship.

According to an embodiment of the present invention, the distillation apparatus used in the case of distilling the esterified reaction oil may be exemplified by a batch simple distillation apparatus, a batch rectification apparatus, a continuous rectification apparatus, a flash evaporation apparatus, a thin film type evaporation apparatus, or the like. In view of attaining the above-described distillation conditions, a thin film type evaporation apparatus is preferred. The thin film type evaporation apparatus is an evaporation apparatus operating in the manner of heating the distillation feed in the state of thin films to evaporate the distillate fraction. The thin film type evaporation apparatus may be exemplified by a centrifuge type thin film distillation apparatus, a falling film type distillation apparatus, a wiped film evaporation apparatus, or the like, in accordance with the method of forming thin films. Among these, it is preferable to use a wiped film evaporation apparatus from the viewpoint of preventing localized overheating to avoid thermal deterioration of oils and fats. The wiped film evaporation apparatus is an apparatus in which the distillation feed is made to run in the form of thin film on the inner side of a cylindrically shaped evaporating surface, and the thin film is agitated with a wiper and heated from the outside, to thus evaporate the distillate fraction. It is preferable for the wiped film evaporation apparatus to employ the format of performing condensation of the distillate fraction with an internal condenser, from the viewpoints of reducing the costs of a vacuum apparatus which lowers the exhaust resistance, and having a large evaporation capacity. As for the wiped film evaporation apparatus, there may be mentioned the "short path distillation apparatus" manufactured by UIC GmbH, "Wipren" manufactured by Shinko Pantec Co., Ltd., "Kontro" manufactured by Hitachi Plant Technologies, Ltd., and the like.

According to an embodiment of the present invention, the composition of the distillate fraction distilled and recovered may vary with the composition of the reaction oil, but it is preferable that the composition approximately includes 5 to 80% by weight of monoacylglycerol, 0.5 to 60% by weight of fatty acids, and 0.5 to 30% by weight of glycerin. It is preferable to determine the amount of raw materials necessary for the subsequent reaction, based on the corresponding composition of the recovered distillate fraction. The reaction conditions thereafter are preferably established to be the same as those of the previous operations.

According to another embodiment of the present invention, it is preferable that the reaction oil obtained after performing the esterification reaction, or the product obtained from distillation thereof, be subsequently subjected to purification according to known methods, so that any residual fatty acids, monoacylglycerol, smelly components and the like are eliminated or decomposed to purify the reaction oil or the distillation product. Furthermore, diacylglycerol may be distilled from the oils and fats rich in diacylglycerol obtained after distillation or after purification as described above, and triacylglycerol or high boiling point components may be eliminated as distillation residues, to thereby obtain oils and fats rich in diacylglycerol with further increased diacylglycerol concentration. In this case, it is preferable that the triacylglycerol and the like recovered as distillation residues, be recycled directly or after being subjected to purification treatment, as a part of the reaction feed, from the viewpoint of effective utilization of raw materials.

It is preferable that the produced oils and fats rich in diacylglycerol contain diacylglycerol in a proportion of preferably 40% by weight or more, more preferably 50% by weight or more, even more preferably 60% by weight or more, even more preferably 65 to 100% by weight, and even more preferably 80 to 98% by weight, in view of having physiological functions such as being less accumulative in the body when used as edible oil.

The present invention includes a process of decreasing an anisidine value of greater than 6 of raw material oils and fats or of the diacylglycerol production intermediates (the diacylglycerol production intermediates will be hereinafter simply described as "intermediates"), by 20% or more. Among these, it is preferable to provide a process of decreasing an anisidine value of greater than 6 of the intermediates by 20% or more, from the viewpoints of suppressing the coloration of oils and fats rich in diacylglycerol, and improving the storage stability. The intermediates include the fatty acids obtained after hydrolysis of the raw material oils and fats, the fatty acids obtained by purifying the resulting fatty acids by distillation or the like, the reaction oil obtained after the esterification reaction of fatty acids and glycerin, the deacidified oil obtained by distilling the reaction oil, the water-washed oil obtained by washing the deacidified oil with water, and the like. Also, in the case of recovering and recycling the unreacted reactants or side products which are eliminated when the reaction oil obtained after the esterification reaction, is distilled to obtain deacidified oil, these unreacted reactants and side products are also included in the intermediates. Among them, for the fatty acids obtained after hydrolyzing the raw material oils and fats, or the fatty acids obtained by purifying the resulting fatty acids by distillation or the like, it is preferable to reduce the anisidine value which is greater than 6, by 20% or more. The reason is that if the object of the treatment to reduce the anisidine value is the fatty acids before the esterification reaction, rather than the raw material oils and fats, or the reaction oil obtained by hydrolyzing the raw material oil sand fats and then esterifying the hydrolysate with glycerin, or the like, then the treatment becomes easier from the viewpoints of having a smaller volume and a lower viscosity. Particularly, in the case of performing an adsorption treatment utilizing an adsorbent as the means for decreasing the anisidine value, it is preferable that the object of the treatment to reduce the anisidine value be fatty acids, from the viewpoint of reducing the amount of use of the adsorbent, and thereby enhancing the yield. Also, in the case of performing the esterification reaction of fatty acids and glycerin by an enzymatic method, it is preferable to reduce the anisidine value of the fatty acids, from the viewpoint of suppressing deterioration of the enzyme.

In view of suppressing coloration of the oils and fats rich in diacylglycerol, and enhancing the storage stability, if the anisidine value of the raw material oils and fats or the intermediates is greater than 6 to 10 or less, it is preferable to render the rate of reduction to be 20% or greater, more preferably 30% or greater, and even more preferably 40% or greater. If the anisidine value is greater than 10 to 15 or less, it is preferable to render the rate of reduction to be 40% or greater, more preferably 50% or greater, and even more preferably 60% or greater. If the anisidine value is greater than 15, it is preferable to render the rate of reduction to be 60% or greater, more preferably 70% or greater, and even more preferably 80% or greater.

Here, the anisidine value is an index indicating the amount of carbonyl compounds which are secondary oxidation products of lipids, and is a value obtained by multiplying the absorption coefficient at 350 nm obtained in the case of reacting the sample with anisidine, by 100. The anisidine value can be measured according to the description in "Anisidine Value (2.5.3-1996)" in "Standard Methods for the Analysis of Fats, Oils, and Related Materials," edited by the Japan Oil Chemists' Society (2003). According to the present invention, it is preferable to have, prior to the process of decreasing the anisidine value by 20% or more, a process of measuring the anisidine value of the raw material oils and fats or the intermediates. Furthermore, it is preferable to select raw material oils and fats or intermediates, which have an anisidine value of greater than 6, through the process of measuring the anisidine value. Moreover, it is also preferable to determine the extent of decreasing the anisidine value based on the previously described standard, according to the numerical ranges of the anisidine value.

Also, according to the present invention, although the anisidine value of the raw material oils and fats or the intermediates before decreasing the anisidine value by 20% or more, is greater than 6, it is more preferable that the anisidine value be 8 or greater, and even more preferably 10 or greater, from the viewpoint that the raw materials or the intermediates can be conveniently preserved. Furthermore, the anisidine value obtained after decreasing the anisidine value is preferably 6 or less, and it is more preferable that the value be 5 or less, even more preferably 4 or less, and even more preferably 0.1 to 3, from the viewpoints of suppressing coloration of the oils and fats rich in diacylglycerol, which are the final products, and of enhanced stability. It is also preferable that the anisidine value of the oils and fats rich in diacylglycerol, which are the final products, be 6 or less, and it is more preferable that the value be 5 or less, even more preferably 4 or less, and even more preferably 0.1 to 3, from the viewpoints of suppression of coloration and enhancement of stability.

Upon producing the oils and fats rich in diacylglycerol, if conventional production processes have been carried out using conventional raw materials, the anisidine value in the raw material oils and fats or the intermediates is 6 or less. However, it was found that in the case where the raw materials are subjected to a special state of preservation or deteriorated during transportation, if such raw materials are used, the anisidine value increases to be greater than 6 during the production processes. For example, if hydrolysis is performed using raw material oils and fats which have been under long-term storage and thus have an elevated peroxide value, the resulting fatty acids may have an elevated anisidine value. Also, even though the raw material oils and fats are not a problem, the fatty acids obtained after hydrolyzing the raw materials, or the intermediates of the esterified reaction oil may have an elevated anisidine value, depending on the state of preservation.

According to an embodiment of the present invention, examples of the means to reduce the anisidine value include adsorption treatment using an adsorbent such as activated clay, activated carbon or silica gel, water wash, distillation, steam deodorization, and the like. Among them, the adsorption treatment using an adsorbent is preferred in view of efficiently reducing carbonyl compounds, which are secondary oxidation products. The method of adsorption treatment may be exemplified by a method of introducing the raw material oils and fats or the intermediates and an adsorbent into a stirring tank, stirring and mixing the mixture, and then filtering the mixture to remove the adsorbent; a method of packing a column with an adsorbent, and passing the raw material oils and fats or the intermediates through the column; or the like. In this case, it is preferable that the object of the treatment to reduce the anisidine value, be the fatty acids obtained after hydrolyzing the raw material oils and fats, or the fatty acids obtained by purifying the resulting fatty acids by distillation or the like, rather than the raw material oils and fats, the reaction oil obtained after subjecting the fatty acids to an esterification reaction with glycerin, the deacidified oil obtained by distilling the reaction oil, the water-washed oil obtained by washing the deacidified oil with water, or the like, from the viewpoint that the weight of use of the adsorbent can be cut down to about 20 to 80%.

According to another embodiment of the present invention, in the case of performing the adsorption treatment using an adsorbent, it is preferable to reduce the water content in the raw material oils and fats or the intermediates in advance, by performing an operation such as placing the materials under reduced pressure conditions, from the viewpoint of efficiently decreasing the anisidine value. The water content of the raw material oils and fats or the intermediates is preferably maintained at 1% or less. Furthermore, it is preferable to prevent the raw material oils and fats or the intermediates from contacting with air during the process of adsorption treatment, in view of enhancing the stability.

In the case of using activated clay as the adsorbent, it is preferable to add the adsorbent in an amount of use of 0.01 to 30 parts by weight, more preferably 0.1 to 20 parts by weight, even more preferably 0.2 to 15 parts by weight, and even more preferably 0.3 to 10 parts by weight, relative to 100 parts by weight of the raw material oils and fats or the intermediates. Also, in the case of using activated clay as the adsorbent, it is preferable not to use a solvent, in terms of costs. The operation temperature is preferably set at 10 to 150° C., more preferably 30 to 105° C., even more preferably 40 to 100° C., and even more preferably 45 to 90° C., at which temperatures the raw material oils and fats or the intermediates do not undergo crystallization. The operation time is preferably set at 1 to 180 minutes, more preferably 2 to 150 minutes, and even more preferably 3 to 120 minutes. As for the operation pressure, it is preferable to perform the treatment under reduced pressure, for example, at 1.33 to 13300 Pa, and more preferably 133 to 2660 Pa. In regard to the activated clay, it is preferable to use a product having a specific surface area measured by the BET method of 100 $m^2/g$ or greater, in view of efficiently decreasing the anisidine value, and it is more preferable to use a product having a specific surface area of 200 to 350 $m^2/g$.

In the case of using activated carbon as the adsorbent, it is preferable to perform the adsorption treatment under the same conditions as in the case of using activated clay. As for the activated carbon, it is preferable to use a product having a decoloration performance measured according to JIS K 1474 of 80% or higher, in view of efficiently decreasing the anisidine value, and it is more preferable to use a product having a decoloration performance of 80 to 99%.

In the case of using silica gel, it is preferable to pack a column with silica gel together with a non-polar solvent such as hexane or petroleum ether, and passing oils and fats, as well as an eluent prepared by mixing a solvent having polarity, such as ethyl ether or ethyl acetate, and a non-polar solvent such as hexane or petroleum ether, through the column. The operation temperature during the column passing operation is preferably set at 10 to 70° C., and more preferably 20 to 50° C., while the retention time is preferably set at 0.3 to 150 minutes, more preferably 0.6 to 120 minutes, and even more preferably 1.0 to 90 minutes.

In the case of performing the adsorption treatment using an adsorbent under reduced pressure, it is preferable to return the pressure inside the apparatus to ambient pressure after the treatment, using a gas having a low oxygen concentration, such as nitrogen gas or carbon dioxide gas.

In view of enhancing the storage stability of the oils and fats rich in diacylglycerol, it is preferable to add tocopherols in an amount of 0.01 to 2.0 parts by weight, more preferably 0.05 to 1.0 parts by weight, and even more preferably 0.1 to 0.5 parts by weight, and/or ascorbic acid palmitate in an amount of 0.001 to 0.5 parts by weight, more preferably 0.005 to 0.1 parts by weight, and even more preferably 0.01 to 0.05 parts by weight, based on 100 parts by weight of the oils and fats rich in diacylglycerol.

EXAMPLES

Analysis Methods (1) Measurement of Fatty Acid Composition

The fatty acid composition was measured by preparing sample fatty acid methyl esters according to the description in "Method of Preparing Fatty Acid Methyl Esters (2.4.1.2-1996)" in "Standard Methods for the Analysis of Fats, Oils, and Related Materials," edited by The Japan Oil Chemists' Society (2003), and measuring the obtained samples according to American Oil Chemists' Society Official Method Ce 1f-96 (GLC method).

(II) Acid Value

The acid value refers to the value expressed in mg of potassium hydroxide necessary for neutralizing the free fatty acids contained in 1 g of a sample according to the description in "Acid Value (2.3.1-1996)" in "Standard Methods for the Analysis of Fats, Oils, and Related Materials," edited by The Japan Oil Chemists' Society (2003).

(III) Diacylglycerol Content

Approximately 10 mg of a sample and 0.5 mL of a trimethylsilylating agent ("Silylating Agent TH", manufactured by Kanto Chemical Co., Inc.) were placed in a glass sample bottle, and the bottle was sealed with a lid, and then heated at 70° C. for 15 minutes. 1.5 mL of water and 1.5 mL of hexane were added to the bottle, and the mixture was shaken. After allowing the mixture to stand, the upper layer was subjected to gas chromatography (GLC) to carry out the analysis of the diacylglycerol content.

(IV) Color

The color was measured according to the description in "Color (Lovibond Method) (2.2.1.1-1996)" in "Standard Methods for the Analysis of Fats, Oils, and Related Materials," edited by The Japan Oil Chemists' Society (2003), with a sample placed in a 5.25-inch cell, and the value was determined from the following formula (2).

$$\text{Color } C = 10R + Y \quad (2)$$

wherein R=Red value, and Y=Yellow value).

(V) Anisidine Value

The anisidine value is an index of the amount of carbonyl compounds which are secondary oxidation products of lipids, which is measured according to the description in "Anisidine Value (2.5.3.-1996)" in "Standard Methods for the Analysis of Fats, Oils, and Related Materials," edited by The Japan Oil Chemists' Society (2003), and refers to the value defined by the absorption coefficient, $E^{1\%}_{1cm}$, at 350 nm, obtained when the sample is subjected to the action of p-methoxyaniline (p-anisidine), multiplied by 100. Furthermore, the decrease rate of the anisidine value was determined according to the following formula (3).

$$\text{Decrease rate of anisidine value} = (A_0 - A_1)/A_0 \times 100$$

wherein the initial anisidine value=$A_0$, and the anisidine value after the reduction treatment=$A_1$.

(VI) Peroxide Value

The peroxide value refers to the value expressed in milliequivalent of iodine liberated per kg of a sample, when potassium iodide is added to the sample according to the description in "Peroxide Value (2.5.2.1-2003)" in "Standard Methods for the Analysis of Fats, Oils, and Related Materials," edited by The Japan Oil Chemists' Society (2003).

(VII) Measurement of Oxidation Stability

The oxidation stability according to the present invention means an induction time (hr) according to the Rancimat method for oils and fats at 120° C. This can be determined according to the description in "CDM Test (2.5.1.2-1996)" in "Standard Methods for the Analysis of Fats, Oils, and Related Materials," edited by The Japan Oil Chemists' Society (2003). That is, using an automated oil and fat stability test apparatus, Rancimat 679 type (Metrohm-Shibata Co., Ltd.), an oil and fat sample is contacted with clean air in a vessel while being heated to 120° C., and the volatile materials generated by oxidation are collected under water. Then, the time (hr) taken to reach the bending point where the conductivity of the water abruptly changes, is measured as the value of oxidation stability. If this amount of time is large, the oxidation stability may be judged to be high.

(VIII) Hydroxyl Value

The hydroxyl value refers to the value expressed in mg of potassium hydroxide necessary for neutralizing acetic acid that is needed to acetylate free hydroxyl groups contained in 1 g of a sample, according to the description in "Hydroxyl Value (2.3.6.2-1996)" in "Standard Methods for the Analysis of Fats, Oils, and Related Materials," edited by The Japan Oil Chemists' Society (2003).

(IX) Melting Point

The melting point was determined based on the temperature at which a sample turns to a completely transparent liquid when heated in a capillary tube, according to the description in "Melting Point (Clear Melting Point) (3.2.2.1-1996)" in "Standard Methods for the Analysis of Fats, Oils, and Related Materials," edited by The Japan Oil Chemists' Society (2003).

(X) Measurement of Water Content in Immobilized Enzyme

The water content in an immobilized enzyme was measured using AQUACOUNTER AQ-7 (Hiranuma Sangyo Co., Ltd.).

[Oven Heating Test]

50 g of a test oil prepared by adding 0.025% by weight of ascorbic acid palmitate (manufactured by DSM Nutrition Corp.) and 0.2% by weight of mixed tocopherols (DE-CANOX MTS-60S, manufactured by ADM Company), was placed in a beaker having a volume of 500 mL (internal diameter 85 mm), and was left to stand still in a light-shielded, forced convection type electrical oven at 80° C. After the standing, the time taken, in days, to the coloration of the test oil, and the peroxide value after 5 days were measured. The beaker was observed from above, and the time point at which the Lab values exceeded the values of L: 80, a: −5 and b: 80 of the reference color, was taken as the time in days taken to the coloration of the test oil. The thickness of the test oil at the time of the observation of color was 12 mm.

[Preparation of Immobilized Enzyme]

<Immobilized Lipase AY>

1000 g of Duolite A-568 (manufactured by Rohm & Haas Company), as a carrier, was stirred for 1 hour in 10 L of a 0.1 N aqueous solution of sodium hydroxide. Then, the carrier was washed with 10 L of distilled water for 1 hour, and was subjected to pH equilibration for 2 hours, using 10 L of a 500 mM phosphate buffer solution (pH 7). Subsequently, pH equilibration was carried out two times for 2 hours each, with 10 L of a 50 mM phosphate buffer solution (pH 7). Thereafter, the carrier was recovered by filtration, and then was subjected to ethanol substitution for 30 minutes with 5 L of ethanol.

After filtering the carrier, 5 L of an ethanol solution having 1000 g of soybean fatty acids dissolved therein was added thereto, and the resulting mixture was stirred for 30 minutes. Then, the carrier was recovered by filtration, and then the carrier was washed 4 times with 5 L of a 50 mM phosphate buffer solution (pH 7) to remove ethanol. Then, the carrier was recovered by filtration. Thereafter, the carrier was contacted with 20 L of a 10 wt % solution of a commercially available lipase (Lipase AY, "Amano" 30G, Amano Enzyme, Inc.) for 4 hours, which acts on oils and fats, to obtain an immobilized enzyme. Furthermore, the immobilized lipase was recovered by filtration, and was washed with 5 L of a 50 mM phosphate buffer solution (pH 7), to remove any unimmobilized lipase or protein. The above-described operations were all carried out at a temperature of 20° C. Thereafter, 4000 g of deodorized soybean oil was added to the immobilized enzyme, the mixture was stirred at a temperature of 40° C. for 10 hours, and then the enzyme was separated from the deodorized soybean oil by filtration. Then, the operation of adding 5 L of hexane, stirring the mixture for 30 minutes, and then separating the hexane layer by filtration, was carried out three times. Subsequently, the solvent was removed at a temperature of 40° C. for 1 hour using an evaporator, and solvent removal was further carried out by drying under reduced pressure for 15 hours under the conditions of a temperature of 40° C. and a pressure of 1300 Pa, to obtain immobilized lipase AY. The water content of the immobilized lipase AY was 2.5% by weight.

[Raw Material Oils and Fats]

As the raw material oils and fats, the oils and fats indicated in Table 1 and Table 2 were used. The measurement of the fatty acid content in the raw material oils and fats, fatty acid composition, glyceride composition, color, anisidine value and peroxide value was carried out by the methods previously described, and the measured values are presented in Table 1 and Table 2.

[Preparation of Fatty Acids]

<Soybean Fatty Acids>

The undeodorized soybean oil indicated in Table 1 and Table 2 was hydrolyzed by the above-described enzymatic method using an immobilized enzyme. To a 30-L jacketed stirring tank equipped with an anchor blade (200 mm×200 mm), 8000 g of undeodorized soybean oil was introduced. The temperature of the jacket water was set to 40° C., and while stirring the oil at 60 r/min, 400 g on a dry basis of an immobilized enzyme was introduced. Subsequently, 4800 g of distilled water warmed to 40° C. was introduced to perform a hydrolysis reaction. Also, for the meantime, the inside of the 30-L jacketed stirring tank was in a nitrogen atmosphere.

After 24 hours from the initiation of reaction, the immobilized enzyme was separated by filtration from the reaction liquid, and the reaction liquid was centrifuged at a speed of rotation of 5000 r/min for 10 minutes to remove the sweet water layer. The water layer was subjected to dehydration under reduced pressure at a temperature of 70° C. and a degree of vacuum of 400 Pa for 30 minutes, to thus obtain soybean fatty acids. The measured values of the fatty acid content, fatty acid composition, glyceride composition, color, anisidine value and peroxide value are presented in Table 4 and Table 5.

<Soybean Liquid Fatty Acids>

The soybean fatty acids indicated in Table 4 and Table 5 were subjected to dry fractionation using polyglycerin fatty acid esters. To a 10-L four-necked glass flask equipped with a triple stirring blade of 125 mm in length, 6000 g of the soybean fatty acids indicated in Table 4 and Table 5, and 12 g of the polyglycerin fatty acid esters indicated in Table 3 were added, and the mixture was homogeneously dissolved at 60° C., which is a temperature higher than the clear melting point of the polyglycerin fatty acid esters. Subsequently, while stirring at 60 r/min, the solution was cooled at a rate of 2° C./hr to reach −3° C., and was maintained for 2 hours to obtain a slurry. Subsequently, the obtained slurry was filtered under

TABLE 1

[Analytical values of raw material oils and fats]

| | Fatty acid [wt %] | GLY [wt %] | MAG [wt %] | DAG [wt %] | TAG [wt %] | Peroxide value [meq/kg] | Anisidine value [−] | Color Red | Yellow | 10R + Y |
|---|---|---|---|---|---|---|---|---|---|---|
| Soybean oil | 0.0 | 0.0 | 0.0 | 1.2 | 98.7 | 0.0 | 2.0 | 2.2 | 25 | 47 |
| Rapeseed oil | 0.3 | 0.0 | 0.0 | 1.3 | 98.4 | 0.0 | 1.7 | 2.8 | 22 | 50 |

GLY: Glyerin
MAG: Monoacylglycerol
DAG: Diacylglycerol
TAG: Triacylglycerol

TABLE 2

[Analytical values of raw material oils and fats]

| | C14 [wt %] | C16 [wt %] | C18 [wt %] | C18:1 [wt %] | C18:2 [wt %] | C18:3 [wt %] | C20 [wt %] | C20:1 [wt %] | C22 [wt %] | C22:1 [wt %] | C24 [wt %] | Average molecular weight |
|---|---|---|---|---|---|---|---|---|---|---|---|---|
| Soybean oil | 0.1 | 10.6 | 4.4 | 23.9 | 52.4 | 7.1 | 0.3 | 0.2 | 0.4 | 0.0 | 0.1 | 278.9 |
| Rapeseed oil | 0.1 | 4.1 | 1.8 | 60.5 | 19.6 | 10.6 | 0.6 | 1.3 | 0.4 | 0.0 | 0.1 | 281.5 | pressure at 0.03 MPa using a nylon filter cloth NY1260D (Nakao Filter Media Corp.), to obtain soybean liquid fatty acids. The measured values of the fatty acid content, fatty acid composition, glyceride composition, color, anisidine value and peroxide value are presented in Table 4 and Table 5.

TABLE 3

| Polyglycerin fatty acid esters | | | | | | | |
|---|---|---|---|---|---|---|---|
| C12 [wt %] | C14 [wt %] | C16 [wt %] | C18 [wt %] | C18:1 [wt %] | Acid value [mg-KOH/g] | Hydroxyl value [mg-KOH/g] | Melting point [° C.] |
| 20 | 5 | 25 | 30 | 20 | 6 | 48 | 37 |

<Rapeseed Fatty Acids>

The undeodorized rapeseed oil indicated in Table 1 and Table 2 was hydrolyzed by the same method as in the case of the soybean fatty acids, to thus obtain rapeseed fatty acids. The measured values of the fatty acid content, fatty acid composition, glyceride composition, color, anisidine value and peroxide value are presented in Table 4 and Table 5.

<Soybean/Rapeseed Mixed Fatty Acids>

3500 g of the soybean liquid fatty acids indicated in Table 4 and Table 5, and 1500 g of rapeseed fatty acids were mixed to obtain soybean/rapeseed mixed fatty acids. The measured values of the fatty acid content, fatty acid composition, glyceride composition, color, anisidine value and peroxide value are presented in Table 4 and Table 5.

<Fatty Acids (Sample A)>

The soybean/rapeseed mixed fatty acids indicated in Table 4 and Table 5 were distilled under the operation conditions of a heater temperature of 200° C., a pressure of 1 to 2 Pa, and a flow rate of 200 mL/min, using a Wiped Film Evaporation Apparatus (Shinko Pantec Co., Ltd., 2-03 type, internal diameter 5 cm, heat transfer area 0.03 m$^2$), to obtain sample A. The measured values of the fatty acid content, fatty acid composition, glyceride composition, color, anisidine value and peroxide value are presented in Table 4 and Table 5.

<Fatty Acids (Sample B)>

The undeodorized soybean oil and undeodorized rapeseed oil indicated in Table 1 and Table 2 were introduced into a 20-L resin vessel, in an amount of 10 kg respectively, and the mixture was transported and stored at 30° C. The peroxide value after 2 months was 7.7 [meq/kg] for the undeodorized soybean oil, and 8.5 [meq/kg] for the undeodorized rapeseed oil. Furthermore, the respective oils and fats were hydrolyzed by the enzymatic method in the same manner as in the above-described production method for Sample A, and only the soybean fatty acids were dry fractionated. Subsequently, the soybean liquid fatty acids and the rapeseed fatty acids were mixed at a ratio of 70% to 30%, and the mixture was distilled to obtain Sample B. The measured values of the fatty acid content, fatty acid composition, glyceride composition, color, anisidine value and peroxide value are presented in Table 4 and Table 5.

TABLE 4

| [Analytical values of fatty acids] | | | | | | | | | |
|---|---|---|---|---|---|---|---|---|---|
| | Fatty acids [wt %] | GLY [wt %] | MAG [wt %] | DAG [wt %] | TAG [wt %] | Peroxide value [meq/kg] | Anisidine value [−] | Color | | |
| | | | | | | | | Red | Yellow | 10R + Y |
| Soybean fatty acids | 91.8 | 0.0 | 0.5 | 4.1 | 3.6 | 0.0 | 1.6 | 3.0 | 20 | 50 |
| Soybean liquid fatty acids | 89.9 | 0.0 | 0.7 | 4.7 | 4.7 | 0.0 | 2.0 | 3.0 | 22 | 52 |
| Rapeseed fatty acids | 91.1 | 0.0 | 0.5 | 4.4 | 4.0 | 0.0 | 2.6 | 3.7 | 16 | 53 |
| Soybean liquid/Rapeseed 7/3 mixed fatty acids | 90.3 | 0.0 | 0.6 | 4.6 | 4.5 | 0.0 | 2.5 | 3.1 | 21 | 52 |
| Sample A | 99.2 | 0.0 | 0.8 | 0.0 | 0.0 | 0.0 | 1.7 | 0.1 | 2 | 3 |
| Sample B | 99.6 | 0.0 | 0.4 | 0.0 | 0.0 | 2.1 | 17.0 | 0.1 | 2 | 3 |

TABLE 5

| [Analytical values of fatty acids] | | | | | | | | | | | | |
|---|---|---|---|---|---|---|---|---|---|---|---|---|
| | C14 [wt %] | C16 [wt %] | C18 [wt %] | C18:1 [wt %] | C18:2 [wt %] | C18:3 [wt %] | C20 [wt %] | C20:1 [wt %] | C22 [wt %] | C22:1 [wt %] | C24 [wt %] | Average molecular weight |
| Soybean fatty acids | 0.1 | 10.5 | 4.4 | 24.5 | 51.8 | 7.1 | 0.4 | 0.2 | 0.4 | 0.0 | 0.1 | 279.0 |
| Soybean liquid fatty acids | 0.1 | 2.5 | 0.7 | 27.2 | 60.6 | 7.7 | 0.1 | 0.2 | 0.1 | 0.0 | 0.0 | 280.4 |
| Rapeseed fatty acids | 0.1 | 4.1 | 1.8 | 60.3 | 19.8 | 10.4 | 0.6 | 1.3 | 0.4 | 0.0 | 0.2 | 281.5 |
| Soybean liquid/Rapeseed 7/3 mixed fatty acids | 0.1 | 3.0 | 1.0 | 37.5 | 48.1 | 8.3 | 0.3 | 0.5 | 0.2 | 0.0 | 0.1 | 280.7 |
| Sample A | 0.1 | 2.8 | 0.9 | 37.5 | 48.8 | 8.4 | 0.2 | 0.4 | 0.1 | 0.0 | 0.0 | 280.6 |
| Sample B | 0.0 | 2.7 | 0.9 | 38.1 | 48.8 | 8.2 | 0.2 | 0.4 | 0.1 | 0.0 | 0.0 | 280.6 |

[Purification of Fatty Acids]
<Activated Clay Treatment 1>

To a 200-mL four-necked glass flask, 100 g of the fatty acids (Sample B) indicated in Table 6 were introduced. While stirring at a temperature of 70° C. at 500 r/min, dehydration under reduced pressure was carried out at a degree of vacuum of 400 Pa for 30 minutes. Subsequently, the pressure inside the flask was returned to ambient pressure with nitrogen gas, and 1 g (1%) of activated clay (NV: manufactured by Mizusawa Industrial Chemicals, Ltd.) was introduced therein. An adsorption treatment was performed in a depressurized state at a degree of vacuum of 400 Pa. After 30 minutes, the pressure inside the flask was returned to ambient temperature with nitrogen gas, and the activated clay was separated by filtration to obtain fatty acids (Sample C). Likewise, an adsorption treatment was performed, with the amount of introduction of the activated clay being 2 g (2%) or 5 g (5%) based on 100 g of the fatty acids (Sample B), to obtain fatty acids (Samples D and E). Furthermore, 100 g (10%) of the activated clay, based on 1000 g of the fatty acids (Sample B) indicated in Table 6, was introduced into a 2-L four-necked glass flask, and an adsorption treatment was performed to obtain fatty acids (Sample F). The measured values of the anisidine value, and the decrease rate of the anisidine value are presented in Table 6.

<Activated Clay Treatment 2>

To a 200-mL four-necked glass flask, 100 g of the fatty acids (Sample B) indicated in Table 6 were introduced. While stirring the fatty acids at a temperature of 25° C. at 500 r/min, 1 g (1%) of activated clay was introduced. While passing nitrogen gas, an adsorption treatment was performed. After 30 minutes, the activated clay was separated by filtration, to thus obtain fatty acids (Sample G). Likewise, an adsorption treatment was performed, with the amount of introduction of the activated clay being 2 g (2%), 5 g (5%) or 10 g (10%) based on 100 g of the fatty acids (Sample B), to obtain fatty acids (Samples H, I and J). The measured values of the anisidine value, and the decrease rate of the anisidine value are presented in Table 6.

[Activated Carbon Treatment]

To a 200-mL four-necked glass flask, 100 g of the fatty acids (Sample B) indicated in Table 6 were introduced. While stirring the fatty acids at a temperature of 70° C. at 500 r/min, dehydration under reduced pressure was performed for 30 minutes at a degree of vacuum of 400 Pa. Subsequently, the pressure inside the flask was returned to ambient pressure with nitrogen gas, and 10 g (10%) of activated carbon (MA brand: manufactured by Taihei Chemical Industrial Co., Ltd.) was introduced therein. An adsorption treatment was performed in a depressurized state at a degree of vacuum of 400 Pa. After 30 minutes, the pressure inside the flask was returned to ambient pressure with nitrogen gas, and the activated carbon was separated by filtration, to obtain fatty acids (Sample K). The measured values of the anisidine value and the decrease rate of anisidine value are presented in Table 6.

<Silica Gel Column Adsorbent Treatment>

A silica gel column made of glass ($\phi$30 mm×H 500 mm) was packed with 100 g of silica gel (Wakogel C-200: manufactured by Wako Pure Chemical Industries, Ltd.), which was dispersed in hexane. Subsequently, a hexane solution prepared by dissolving 10 g of the fatty acids (Sample B) indicated in Table 6 in 20 mL of hexane, was passed through the column, and then 500 mL of a mixed solvent of ethyl acetate:hexane=15:85 (volume ratio) was passed through the column, to thereby collect the eluted liquid. The obtained eluent was removed of solvent, to obtain fatty acids (Sample L). Likewise, a silica gel column adsorbent treatment was performed, with the ratio of the mixed solvent at ethyl acetate:hexane=50:50, to obtain fatty acids (Sample M). The measured values of the anisidine value and the decrease rate of anisidine value are presented in Table 6.

TABLE 6

[Purification of DAG production intermediates]

| Sample name | DAG production intermediate | Method of purification | Anisidine value [−] | Decrease rate of anisidine value [%] |
|---|---|---|---|---|
| A | Fatty acid | Untreated | 1.7 | — |
| B | Fatty acid | Untreated | 17.0 | — |
| C | Fatty acid | Activated clay 1% 70° C. 30 min reduced pressure | 9.6 | 44 |
| D | Fatty acid | Activated clay 2% 70° C. 30 min reduced pressure | 6.2 | 64 |
| E | Fatty acid | Activated clay 5% 70° C. 30 min reduced pressure | 3.6 | 79 |
| F | Fatty acid | Activated clay 10% 70° C. 30 min reduced pressure | 2.2 | 87 |
| G | Fatty acid | Activated clay 1% 25° C. 30 min ambient pressure | 16.4 | 4 |
| H | Fatty acid | Activated clay 2% 25° C. 30 min ambient pressure | 15.6 | 8 |
| I | Fatty acid | Activated clay 5% 25° C. 30 min ambient pressure | 13.6 | 20 |
| J | Fatty acid | Activated clay 10% 25° C. 30 min ambient pressure | 12.5 | 26 |
| K | Fatty acid | Activated carbon 10% 70° C. 30 min reduced pressure | 6.8 | 60 |
| L | Fatty acid | Silica gel treatment Ethyl acetate 15% Hexane 85% | 6.8 | 60 |
| M | Fatty acid | Silica gel treatment Ethyl acetate 50% Hexane 50% | 13.6 | 20 |
| N | Deacidified oil | Untreated | 8.5 | — |
| O | Deacidified oil | Activated clay 1% 70° C. 30 min reduced pressure | 6.6 | 22 |
| P | Deacidified oil | Activated clay 2% 70° C. 30 min reduced pressure | 5.8 | 32 |

TABLE 6-continued

[Purification of DAG production intermediates]

| Sample name | DAG production intermediate | Method of purification | Anisidine value [−] | Decrease rate of anisidine value [%] |
|---|---|---|---|---|
| Q | Deacidified oil | Activated clay 5% 70° C. 30 min reduced pressure | 3.3 | 61 |
| R | Deacidified oil | Activated clay 10% 70° C. 30 min reduced pressure | 1.7 | 80 |

[Production of Oils and Fats Rich in Diacylglycerol 1]

The fatty acids indicated in Table 6 (Samples A, B and F) were used to perform an esterification treatment, a deacidification treatment, an acid treatment, a water wash treatment and a deodorization treatment, to thereby produce oils and fats rich in diacylglycerol.

<Esterification Reaction>

To a 2-L four-necked glass flask, 50 g (an amount equivalent to 5% by weight of the sum of the amounts of fatty acids and glycerin) of an immobilized enzyme (Lipozyme RM IM manufactured by Novozymes Japan, Ltd.) was introduced. Subsequently, 861 g of the fatty acids were introduced, after an adjustment of the temperature to 50° C. While stirring the fatty acids at a temperature of 50° C. at 500 r/min, 139 g of glycerin was introduced thereto so that the molar ratio of the fatty acids and glycerin would be 2:1, to thus initiate the reaction. After 1 minute from the initiation of the reaction, the pressure was reduced, and an esterification reaction was carried out for 3 hours at a degree of vacuum of 400 Pa. After the reaction, the immobilized enzyme was separated by filtration, to obtain an esterified reaction oil.

<Deacidification Treatment>

The esterified reaction oil was distilled using a wiped film evaporation apparatus (Shinko Pantec Co., Ltd., 2-03 type, internal diameter 5 cm, heat transfer area 0.03 m$^2$), under the operation conditions of a heater temperature of 230° C., a pressure of 3.3 Pa, and a flow rate of 150 mL/min, to thereby obtain a deacidified oil.

<Acid Treatment>

A 10% aqueous solution of citric acid was added to the deacidified oil in a proportion of 2%, the mixture was mixed at a temperature of 70° C. for 30 minutes at 400 r/min, and then dehydration under reduced pressure was performed for 30 minutes while mixing at a temperature of 70° C. and a degree of vacuum of 400 Pa at 400 r/min, to thus obtain an acid-treated oil.

<Water Wash Treatment>

Distilled water warmed to a temperature of 70° C. was added to the acid-treated oil in a proportion of 10%, and the mixture was vigorously mixed at a temperature of 70° C. for 30 minutes at 600 r/min, and then centrifuged to separate the oil phase. This water wash operation was carried out three times, and dehydration under reduced pressure was performed at a temperature of 70° C. and a degree of vacuum of 400 Pa for 30 minutes, to obtain a water-washed oil.

<Deodorization Treatment>

600 g of the water-washed oil was introduced into a 1-L glass Claisen flask, and then a steam generating apparatus was connected to the 1-L glass Claisen flask through a capillary glass tube having an internal diameter of 2.5 mm, to thereby perform deodorization at a temperature of 245° C. and a pressure of 260 Pa. After 35 minutes, the system was cooled to 70° C., and then nitrogen was blown into the deodorization apparatus to return the pressure to ambient pressure. Thus, a deodorized oil (Samples i, ii and iii) was obtained. The measured values of the fatty acid content, fatty acid composition, glyceride composition, color, anisidine value and peroxide value; the time taken, in days, to coloration due to an oven heating test; and the peroxide value after 5 days are presented in Table 7 and Table 8. Furthermore, the Rancimat value of the deodorized oil prepared using Sample A as the raw material for esterification reaction (Sample i) was 8.2 hours when 200 ppm of mixed tocopherols (DE-CANOX MTS-60S, manufactured by ADM Company) was added to the deodorized oil, and was 0.9 hours when tocopherols were not added.

<Deacidified Oil (Sample N)>

The Sample B indicated in Table 4 and Table 5 was subjected to an esterification reaction by doubling the volume of the reaction vessel and the amount of the raw materials used in the method described in the previous section "Esterification reaction", and the above-described "deacidification treatment" was performed, to thus obtain a deacidified oil (Sample N). The measured values of the fatty acid content, fatty acid composition, glyceride composition, color, anisidine value and peroxide value are presented in Table 9 and Table 10.

<Activated Clay Treatment of Deacidified Oil (Sample N)>

To a 2-L four-necked glass flask, 1000 g of the Sample N indicated in Table 6 was introduced. While stirring the fatty acids at a temperature of 70° C. at 500 r/min, dehydration under reduced pressure was performed for 30 minutes at a degree of vacuum of 400 Pa. Subsequently, the pressure inside the flask was returned to ambient pressure with nitrogen gas, and 10 g (1%) of activated clay (NV: manufactured by Mizusawa Industrial Chemicals, Ltd.) was introduced therein. An adsorption treatment was performed in a depressurized state at a degree of vacuum of 400 Pa. After 30 minutes, the pressure inside the flask was returned to ambient temperature with nitrogen gas, and the activated clay was separated by filtration to obtain Sample O. The measured values of the anisidine value are presented in Table 6, Table 9 and Table 10. Likewise, a 200-mL four-necked glass flask was used, and an adsorption treatment was performed by setting the amount of introduction of the activated clay based on 100 g of the Sample N to be 2 g (2%), 5 g (5%) and 10 g (10%), to thus obtain Samples P, Q and R. The measured values of the anisidine value and the decrease rate of the anisidine value are presented in Table 6.

[Production of Oils and Fats Rich in Diacylglycerol 2]

A deacidified oil obtained by treating the Sample N with activated clay (Sample O) was subjected to an acid treatment, a water wash treatment and a deodorization treatment by the above-described methods, to obtain an deodorized oil (Sample iv). The measured values of the fatty acid content, fatty acid composition, glyceride composition, color, anisidine value and peroxide value; the time taken, in days, to coloration due to an oven heating test; and the peroxide value after 5 days are presented in Table 7 and Table 8.

TABLE 7

[Analytical values of DAG deodorized oil]

| | Fatty acids [wt %] | GLY [wt %] | MAG [wt %] | DAG [wt %] | TAG [wt %] | Peroxide value [meq/kg] | Anisidine value [-] | Color Red | Color Yellow | Color 10R + Y | Days to coloration | Peroxide value after 80° C./5 days [meq/kg] |
|---|---|---|---|---|---|---|---|---|---|---|---|---|
| Sample i (Raw material: Sample A) | 0.0 | 0.0 | 0.2 | 95.6 | 4.1 | 0.0 | 1.1 | 0.1 | 2 | 3 | 7 | 4.0 |
| Sample ii (Raw material: Sample B) | 0.0 | 0.0 | 0.3 | 96.0 | 3.7 | 0.0 | 7.1 | 0.1 | 2 | 3 | 5 | 68.0 |
| Sample iii (Raw material: Sample F) | 0.1 | 0.0 | 0.5 | 94.5 | 4.9 | 0.0 | 1.8 | 0.2 | 2 | 4 | 10 | 1.5 |
| Sample iv (Raw material: Sample O) | 0.1 | 0.0 | 0.3 | 95.6 | 4.0 | 0.0 | 5.3 | 0.2 | 1 | 3 | 7 | 47.0 |

TABLE 8

[Analytical values of DAG deodorized oil]

| | C14 [wt %] | C16 [wt %] | C18 [wt %] | C18:1 [wt %] | C18:2 [wt %] | C18:3 [wt %] | C20 [wt %] | C20:1 [wt %] | C22 [wt %] | C22:1 [wt %] | C24 [wt %] | Average molecular weight |
|---|---|---|---|---|---|---|---|---|---|---|---|---|
| Sample i (Raw material: Sample A) | 0.0 | 2.7 | 0.9 | 38.2 | 48.9 | 8.1 | 0.2 | 0.4 | 0.1 | 0.0 | 0.0 | 280.6 |
| Sample ii (Raw material: Sample B) | 0.1 | 2.8 | 1.1 | 38.2 | 49.4 | 6.8 | 0.2 | 0.6 | 0.1 | 0.0 | 0.0 | 280.7 |
| Sample iii (Raw material: Sample F) | 0.1 | 2.8 | 1.1 | 38.1 | 49.4 | 6.8 | 0.2 | 0.5 | 0.1 | 0.0 | 0.0 | 280.7 |
| Sample iv (Raw material: Sample O) | 0.0 | 2.8 | 0.9 | 38.2 | 48.8 | 8.2 | 0.2 | 0.4 | 0.0 | 0.0 | 0.0 | 280.6 |

TABLE 9

[Analytical values of adsorption treated process intermediates]

| | Fatty acids [wt %] | GLY [wt %] | MAG [wt %] | DAG [wt %] | TAG [wt %] | Peroxide value [meq/kg] | Anisidine value [-] | Color Red | Color Yellow | Color 10R + Y |
|---|---|---|---|---|---|---|---|---|---|---|
| Sample N | 0.1 | 0.0 | 0.3 | 96.7 | 3.0 | 5.3 | 8.5 | 0.2 | 3 | 5 |
| Sample O | 0.1 | 0.0 | 0.1 | 96.8 | 3.0 | 1.3 | 6.6 | 0.2 | 1 | 3 |

TABLE 10

[Analytical values of adsorption treated process intermediates]

| | C14 [wt %] | C16 [wt %] | C18 [wt %] | C18:1 [wt %] | C18:2 [wt %] | C18:3 [wt %] | C20 [wt %] | C20:1 [wt %] | C22 [wt %] | C22:1 [wt %] | C24 [wt %] | Average molecular weight |
|---|---|---|---|---|---|---|---|---|---|---|---|---|
| Sample N | 0.1 | 3.1 | 0.8 | 36.4 | 49.6 | 8.9 | 0.2 | 0.3 | 0.0 | 0.0 | 0.0 | 280.5 |
| Sample O | 0.0 | 2.7 | 0.9 | 37.8 | 49.0 | 8.4 | 0.2 | 0.4 | 0.1 | 0.0 | 0.0 | 280.6 |

What is claimed is:

1. A process for producing an oil or fat rich in diacylglycerol comprising:

subjecting fatty acids which are obtainable by hydrolyzing raw material oils and fats and having an anisidine value of greater than 6 to an adsorption treatment, wherein the anisidine value is decreased by 20% or more, and subjecting said fatty acids decreased in anisidine value to an esterification reaction with glycerin.

2. The process according to claim 1, wherein the adsorption treatment utilizes activated clay.

3. The process according to claim 2, wherein the adsorption treatment is performed under reduced pressure.

4. The process according to claim 1, further comprising measuring the anisidine value of said fatty acids, prior to the decreasing the anisidine value by 20% or more.

5. The process according to claim 4, wherein said fatty acids having an anisidine value of greater than 6 are selected by the step of measuring the anisidine value.

6. The process according to claim 1, wherein the esterification reaction is carried out by an enzymatic method.

7. The process according to claim 6, wherein the ratio of the number of moles of glycerin to the number of moles of fatty acids is 1 to 3.

8. The process according to claim 7, wherein the ratio is 1.5 to 2.5.

9. The process according to claim 1, wherein the oil or fat rich in diacylglycerol contains diacylglycerol in a proportion of 40% by weight or more.

10. The process according to claim 1, wherein the oil or fat rich in diacylglycerol contains diacylglycerol in a proportion of 80 to 98% by weight.

11. The process according to claim 1, wherein the anisidine value is greater than 6 and less than 10, and the value is decreased by 40% or more.

12. The process according to claim 1, wherein the anisidine value is greater than 10 and less than 15, and the value is decreased by 60% or more.

13. The process according to claim 1, wherein the anisidine value is greater than 15, and the value is decreased by 80% or more.

14. The process according to claim 1, wherein the anisidine value is 10 or more, and is decreased to a value of 0.1 to 3.

* * * * *